US009199904B2

(12) United States Patent
Desrosiers et al.

(10) Patent No.: US 9,199,904 B2
(45) Date of Patent: Dec. 1, 2015

(54) PROCESS FOR PREPARING CARBOXYLIC ACIDS

(75) Inventors: Jean-Nicolas Desrosiers, Southbury, CT (US); Joe Ju Gao, Southbury, CT (US); Jason Alan Mulder, New Milford, CT (US); Jinhua J. Song, Hopewell Junction, NY (US); Xingzhong Zeng, New Milford, CT (US)

(73) Assignee: BOEHRINGER INGELHEIM INTERNATIONAL GMBH, Ingelheim Am Rhein (DE)

( * ) Notice: Subject to any disclaimer, the term of this patent is extended or adjusted under 35 U.S.C. 154(b) by 0 days.

(21) Appl. No.: 14/005,393

(22) PCT Filed: Mar. 15, 2012

(86) PCT No.: PCT/US2012/029155
§ 371 (c)(1),
(2), (4) Date: Feb. 7, 2014

(87) PCT Pub. No.: WO2012/129037
PCT Pub. Date: Sep. 27, 2012

(65) Prior Publication Data
US 2015/0038731 A1 Feb. 5, 2015

Related U.S. Application Data

(60) Provisional application No. 61/454,030, filed on Mar. 18, 2011.

(51) Int. Cl.
C07C 51/16 (2006.01)
C07C 51/09 (2006.01)
C07C 51/02 (2006.01)
C07C 51/41 (2006.01)
C07C 51/43 (2006.01)
C07C 57/58 (2006.01)
C07C 57/62 (2006.01)
C07C 43/176 (2006.01)
C07C 69/65 (2006.01)
C07F 7/18 (2006.01)

(52) U.S. Cl.
CPC ............. C07C 51/09 (2013.01); C07C 43/176 (2013.01); C07C 51/02 (2013.01); C07C 51/412 (2013.01); C07C 51/43 (2013.01); C07C 57/58 (2013.01); C07C 57/62 (2013.01); C07C 69/65 (2013.01); C07F 7/1868 (2013.01); C07B 2200/07 (2013.01)

(58) Field of Classification Search
CPC ...... A01B 12/006; C07C 69/65; C07C 57/58; C07C 57/60; C07C 57/62; C07F 7/1868
USPC ............. 562/412, 493; 560/103; 568/28
See application file for complete search history.

(56) References Cited

FOREIGN PATENT DOCUMENTS

| DE | 19530205 A1 | 2/1997 |
| WO | 0212155 A2 | 2/2002 |
| WO | WO2012/024150 * | 2/2012 |

OTHER PUBLICATIONS

Beaulieu, Christian et al. "Efficient synthesis of optically active 2-arylalkanoic acids" Tetrahedron Letters 40 (1999) pp. 1637-1640.
Bonati, A. et al. "Dialkylaminoethyl esters of substituted phenylacetic and alpa-phenylbutric acid" Chemical Abstract Service; Accession No: 1960:1956, XP-002678342, 4 pgs.
Cramer, Friederich et al. "Inclusion compounds. XVII. Catalysis of decarboxylation by cyclodextrins. A model reaction for the mechanism of enzymes." Chemical Abstract Service; Accession No: 1965:60334, XP-002678341, 1 pg.
Fujio, Mizue et al. "Substituent effect on the acetolysis of neophyl p-bromobenzenesulfonates" Chemical Abstract Service; Accession No: 1985:5305, XP-002678340, 1 pg.
International Search Report for PCT/US2012/029155 mailed on Jul. 20, 2012.
Noji, Masahiro et al. "A Novel Synthetic Route to 2-Arylalkanoic Acids by a Ruthenium-Catalyzed Chemoselective Oxidation of Furan Rings" Synthesis (2008) No. 23, pp. 3835-3845.
Stivala, Daniel et al. "Azaindoles as potent CRTH2 receptor antagonists" Chemical Abstracts Service, Accession No. 2011:40730, XP-002678338, 2 pgs.
Stivala, Craig E. et al. "Highly enantioselective direct alkylation of arylacetic acids with chiral lithium amides as traceless auxiliaries." Chemical Abstracts Service; Accession No: 2011:886861, XP-002678337, 2 pgs.
Wang, Dong-Hui et al. "Versatile Pd (II) -Catalyzed C-H Avtivation/Aryl-Aryl Couplings of Benzoic and Phenyl Acetic Acids" Chemical Abstracts Service; Accession No: 2008:1500801, XP-002678339, 2 pgs.

* cited by examiner

Primary Examiner — Yevegeny Valenrod
Assistant Examiner — Blaine G Doletski
(74) Attorney, Agent, or Firm — Michael P. Morris; Usha R. Patel

(57) ABSTRACT

The present invention relates to a process of making a compound of formula (XII) or (XIIA): wherein $R^1, R^2, R^4$ and X are as defined herein.

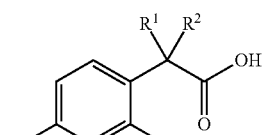

XII

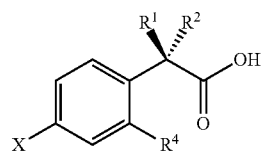

XIIA

9 Claims, No Drawings

PROCESS FOR PREPARING CARBOXYLIC ACIDS

This application relates to a process of preparing chiral carboxylic acids which are precursors for the synthesis of nitriles. These nitriles can be used to prepare pharmaceutically active compounds, such as FLAP inhibitors, containing an oxadiazole ring.

BACKGROUND OF THE INVENTION

Carboxylic acids may be converted to nitriles by methods known in the literature. These nitrile intermediates can be used to prepare oxadiazole compounds which are inhibitors of five lipoxygenase activating protein (FLAP) and are thus useful for treating a variety of diseases and disorders that are mediated or sustained through the activity of leukotrienes including asthma, allergy, rheumatoid arthritis, multiple sclerosis, inflammatory pain, acute chest syndrome and cardiovascular diseases including atherosclerosis, myocardial infarction and stroke. The preparation of oxadiazole compounds via a nitrile intermediate is disclosed in WO2012024150, "Oxadiazole Inhibitors of Leukotriene Production".

DESCRIPTION OF THE INVENTION

The present invention is directed to a process of making a compound of formula XII or XIIA:

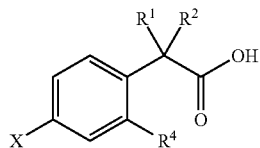

XII

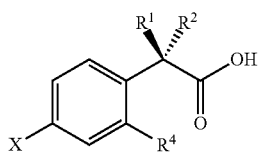

XIIA the process comprising:

a) reacting a carbonyl compound of formula XIII with a base and a $C_1$-$C_3$ alkylating agent, in a suitable solvent, to provide a compound of formula XIV:

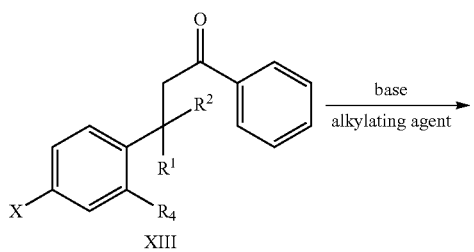

XIII

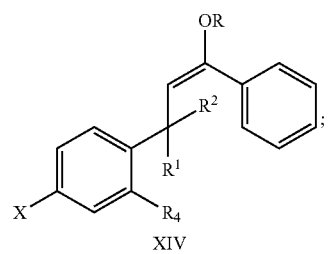

XIV b) reacting the compound of formula XIV with ozone, in a suitable solvent, followed by reaction with a dehydrating agent in the presence a base to provide an ester of formula XV;

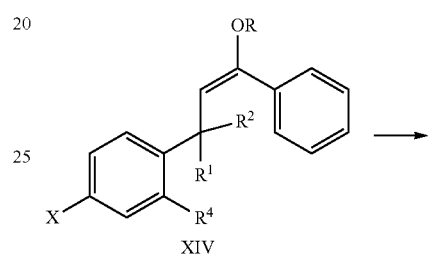

c) hydrolyzing the ester of formula XV, in a suitable solvent, in the presence of a suitable base, to provide an acid of formula XII:

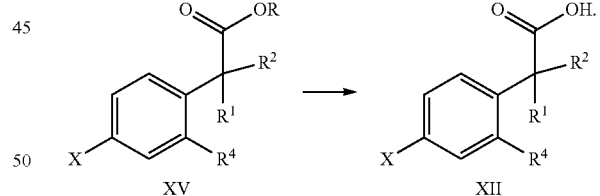

and d) optionally resolving the racemic acid of formula XII to provide the enantiomers XIIA and XIIA'.

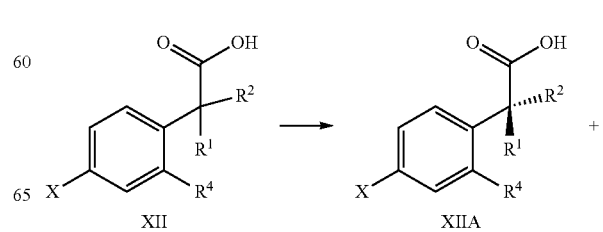

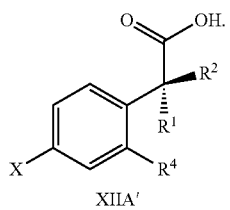

d') Alternatively, the acid XII obtained in step c) may be reacted with an organic base, such as a primary or secondary amine, in a suitable solvent, to provide the corresponding salt of formula XVI.

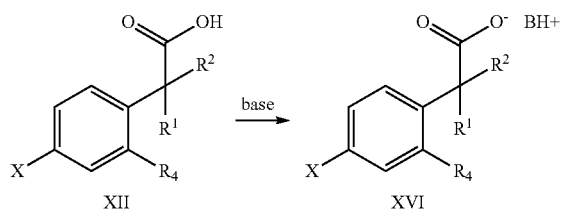

wherein:

R in step a) is a $C_{1-3}$ alkyl provided by the $C_1$-$C_3$ alkylating agent;

$R^1$ and $R^2$ are each independently hydrogen, $C_{1-7}$ alkyl or $C_{3-10}$ carbocycle, with the proviso that both $R^1$ and $R^2$ are not hydrogen;

$R^4$ is hydrogen, $C_{1-3}$ alkyl, halogen or nitrile; and

X is halogen.

B in step d') is a primary or secondary amine.

Alternatively, reacting a carbonyl compound of formula XIII with a fluoride source and ethyl trimethylsilyl acetate, in a suitable solvent, provides a trimethyl silyl enol ether of formula XVII. This TMS ether may be converted to the acid of formula XII or XIIA via steps b), c), and d).

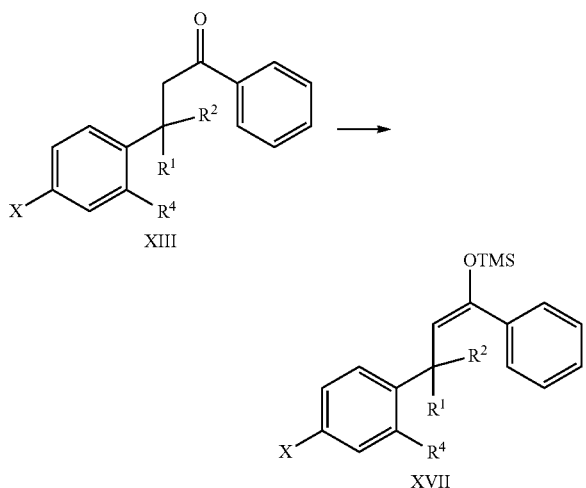

Non-limiting examples of bases useful in step (a) include potassium t-butoxide, sodium t-butoxide, lithium t-butoxide, sodium hydride, potassium hydride, lithium hydride, sodium hexamethyldisilazide, potassium hexamethyldisilazide, lithium hexamethyldisilazide, sodium methoxide, potassium methoxide, lithium methoxide, sodium ethoxide, potassium ethoxide, lithium ethoxide, LDA, n-butyllithium, sec-butyllithium or t-butyllithium. Non-limiting examples of solvents useful for step (a) include dimethylformamide, dichloromethane, ethyl acetate, hexane, heptane, acetonitrile, methyl tert-butyl ether, isopropyl acetate, toluene, and cyclopropylmethyl ether. Non-limiting examples of alkylating agents useful in step (a) include dimethyl sulfate, dimethyl carbonate, bromomethane, methyl trifluoromethanesulfonate and iodomethane. Non-limiting examples of silylating agents useful in step (a) include trimethylchlorosilane, tert-butyldimethylchlorosilane, triphenylchlorosilane, and triisopropylchlorosilane, triethylchlorosilane.

Non-limiting examples of solvents useful in step (b) include dimethylformamide, dichloromethane, ethyl acetate, hexane, heptane, acetonitrile, methyl tert-butyl ether, isopropyl acetate, toluene, and cyclopropylmethyl ether. Non-limiting examples of bases useful in step (b) include 1,8-diazabicycloundec-7-ene (DBU), triethylamine, pyridine, 4-methylmorpholine, diisopropylethylamine and dimethylamine. Non-limiting examples of dehydrating agents useful in step (b) include acetic anhydride, methanesulfonyl chloride, trifluoroacetic anhydride, toluenesulfonyl chloride, sodium hypochlorite, calcium hypochlorite and tert-butyl hypochlorite.

Non-limiting examples of bases useful in step (c) include potassium hydroxide, sodium hydroxide, lithium hydroxide and cesium hydroxide. Non-limiting examples of solvents useful in step (c) include methanol, methanol-water mixture, dimethylformamide, dichloromethane, ethyl acetate, hexane, heptane, acetonitrile, methyl tert-butyl ether, isopropyl acetate, toluene, and cyclopropylmethyl ether.

The resolution of the racemic acid of formula XII described in optional step d) can be carried out using methods known in the art including, for example, fractional crystallization, chiral chromatography and using chiral amine resolving agents.

The carboxylic acid of formula XII or XIIA may be converted to a nitrile of formula VII as outlined in Scheme A below.

Scheme A

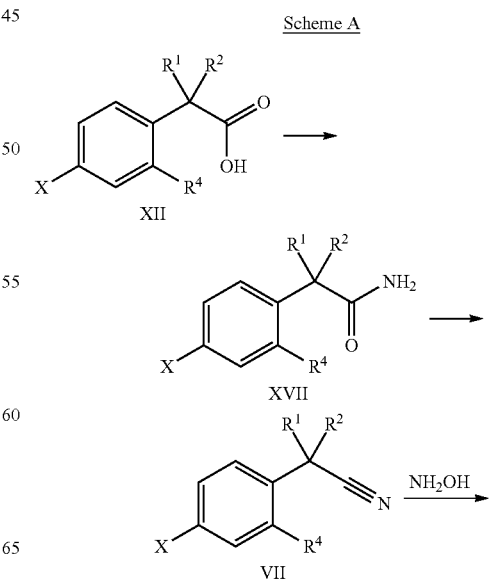

-continued

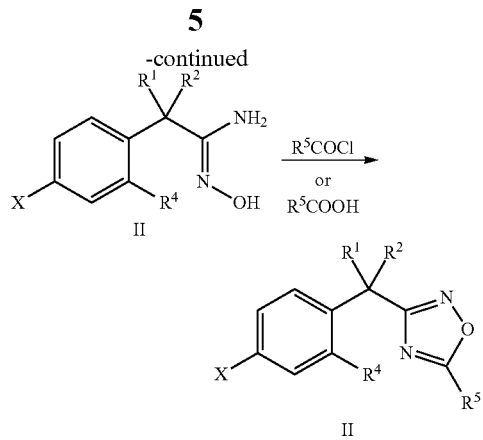

As illustrated in scheme A, reaction of a carboxylic acid of XII with a reagent such as thionyl chloride, followed by a reagent such as ammonia, in a suitable solvent, provides an amide of formula XVII. Reaction of the amide of formula XVII with a suitable dehydrating agent, in a suitable solvent, provides a nitrile of formula VII. Reaction of the compound of formula VII with hydroxylamine, under standard reaction conditions, provides a compound of formula VIII. Reaction of the compound of formula VIII with an acid chloride $R^5COCl$, in a suitable solvent, in the presence of a suitable base, provides an oxadiazole compound of formula II wherein $R^5$ is $C_{1-6}$ alkyl, $C_{3-10}$ carbocycle, 5-11 membered heterocycle, aryl, 5-11 membered heteroaryl, —C(O)—$R^6$, hydroxy or —$NR^7R^8$, wherein each $R^5$ is optionally independently substituted with one to three groups selected from $R^9$, $R^{10}$ and $R^{11}$;

$R^6$ is $C_{3-8}$ heterocycle or —NH-5-6 membered heterocycle, each optionally independently substituted with one to three groups selected from $R^9$, $R^{10}$ and $R^{11}$;

$R^7$ and $R^8$ are each independently hydrogen or $C_{1-6}$ alkyl;

$R^9$, $R^{10}$ and $R^{11}$ are independently selected from
  (a) —H,
  (b) —OH,
  (c) halogen,
  (d) —CN,
  (e) —$CF_3$,
  (f) $C_{1-6}$alkyl optionally substituted with one to three —OH, —$N(R^{12})(R^{13})$, 3-6 membered heterocycle, $C_{1-6}$alkoxy, —$C(O)N(R^{12})(R^{13})$ or —$S(O)_nC_{1-6}$alkyl,
  (g) $C_{1-6}$alkoxy,
  (h) —$N(R^{12})(R^{13})$,
  (i) —$S(O)_nC_{1-6}$alkyl,
  (j) —$CO_2R^{12}$,
  (k) —$C(O)N(R^{12})(R^{13})$,
  (l) —$S(O)_2N(R^{12})(R^{13})$,
  (m) a 3-10 membered heterocyclic group optionally substituted with one to three $C_{1-6}$ alkyl groups,
  (n') oxo,
  (o) —C(O)—$C_{1-3}$ alkyl;

$R^{12}$ and $R^{13}$ are each independently selected from —H, —$C_{1-6}$alkyl, $C(O)C_{1-6}$alkyl, and a 3-6 membered heterocyclic group, each of which is optionally independently substituted with one to three $C_{1-6}$alkyl groups, —OH, $C_{1-6}$alkoxy, —$C(O)N(R^{14})(R^{15})$, —$S(O)_nC_{1-6}$alkyl, CN, a 3-6 membered heterocyclic group, —$OC_{1-6}$alkyl, $CF_3$, or;

$R^{12}$ and $R^{13}$ taken together with the nitrogen ring to which they are attached form a heterocyclic ring optionally substituted with one to three —OH, CN, —$OC_{1-6}$alkyl or oxo;

$R^{14}$ and $R^{15}$ are each independently selected from —H and —$C_{1-6}$alkyl;

n is 0, 1 or 2;

Alternatively, reaction of a compound of formula VIII with an acid $R^5COOH$, in a suitable solvent, in the presence of carbonyl diimidazole, or other suitable amide coupling reagent, provides an oxadiazole compound of formula II which can then be converted to oxadiazole FLAP inhibitors disclosed in WO2012024150, "Oxadiazole Inhibitors of Leukotriene Production".

The invention relates to the use of any compounds described above containing one or more asymmetric carbon atoms including racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form.

The invention includes methods using all such tautomers.

All terms as used herein in this specification, unless otherwise stated, shall be understood in their ordinary meaning as known in the art. For example, "$C_{1-6}$alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —$S(O)_2$—$C_{1-6}$ alkyl.

The term "$C_{3-10}$ carbocycle" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl(decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$C_{6-10}$ aryl" or "aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, tetrahydropyranyl, oxetanyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

General Synthetic Methods

The invention provides processes for making compounds of Formula (XII) and (XIIA) wherein unless specified otherwise, R$^1$, R$^2$, R$^4$, R, B and X in the Formulas below shall have the meaning of R$^1$, R$^2$, R$^4$, R, B and X in Formula (XII) and (XIIA) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, recrystallization and/or preparative HPLC.

The example which follows is illustrative and, as recognized by one skilled in the art, particular reagents or conditions could be modified as needed for individual compounds without undue experimentation. Starting materials and intermediates used, in the Scheme below, are either commercially available or easily prepared from commercially available materials by those skilled in the art.

Scheme 6

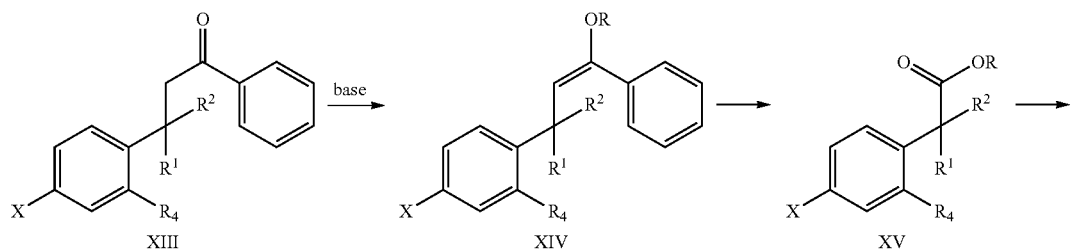

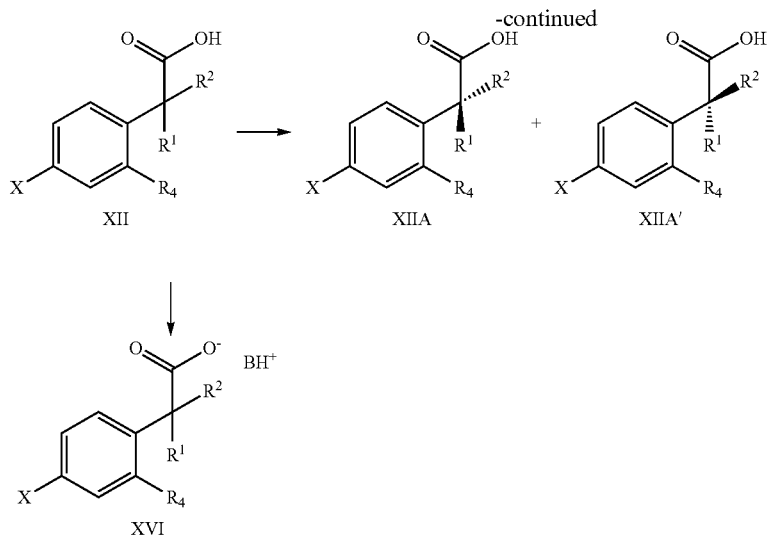

As illustrated in scheme 6, reaction of a ketone of formula XIII with methylating agent in the presence of a suitable base, in a suitable solvent, provides an enolether of formula XIV. Reaction of the enolether XIV with an oxidizing agent such as ozone, under suitable conditions, provides an ester of formula XV. Hydrolysis of the ester of formula XV, in a suitable solvent, in the presence of a suitable base, provides an acid of formula XII. This racemic acid may be resolved to provide the enantiomers XIIA and XIIA'. Alternatively, the acid XII may be reacted with an organic base such as a primary or secondary amine, in a suitable solvent, to provide the corresponding salt.

SYNTHETIC EXAMPLE

Example 1

Synthesis of 2-(4-Bromo-phenyl)-2-cyclopropyl-propionic acid

[(E)-3-(4-Bromo-phenyl)-3-Cyclopropyl-1-phenyl-but-1-enyloxy]-trimethylsilane

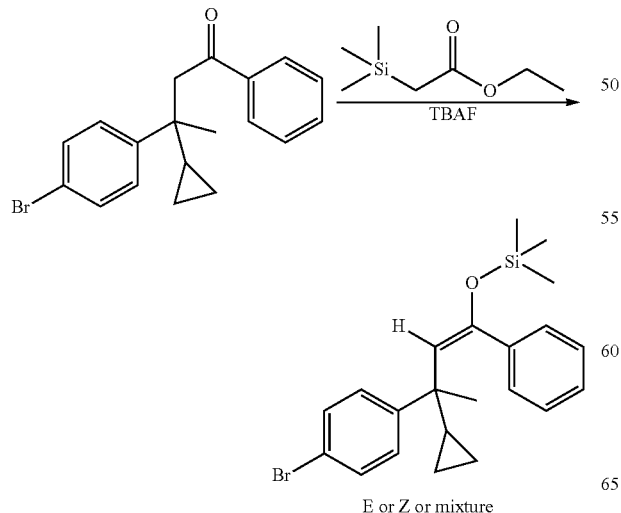

A 25 mL flask is charged with 3-(4-Bromo-phenyl)-3-cyclopropyl-1-phenyl-butan-1-one (3.0 g, 8.2 mmol) and ethyl trimethylsilyl acetate (7.58 mL, 41 mmol). At 20° C., tetrabuylammonium fluoride (TBAF) (41 uL, 0.04 mmol) is added. After stirring for 15 minutes, the mixture is concentrated to minimum volume; this is followed by further removal of volatiles by high vacuum pump yielding the desired silyl enol ether[(E)-3-(4-Bromo-phenyl)-3-cyclopropyl-1-phenyl-but-1-enyloxy]-trimethylsilane as a brown oil (3.41 g, 80 wt %, 82% yield).

Bromo-4-((E)-1-cyclopropyl-3-methoxy-1-methyl-3-phenyl-allyl)-benzene

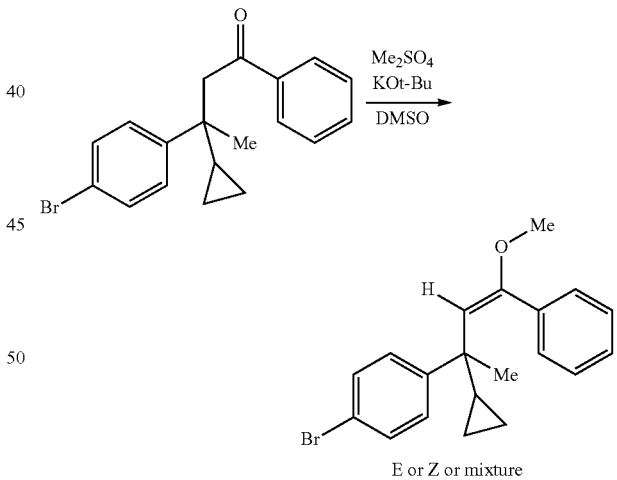

A 250 mL reaction vessel is charged with anhydrous dimethyl sulfoxide (DMSO) (30 mL) followed by potassium tert-butoxide (KOt-Bu) (3.16 g, 28 mmol, 1.5 equiv) at 25±5° C. A solution of the ketone 3-(4-Bromo-phenyl)-3-cyclopropyl-1-phenyl-butan-1-one (7.5 g, 85.9 wt %, 18.78 mmol) in anhydrous DMSO (30 mL) is added at 25±5° C. The reaction mixture is agitated at 25±5° C. for at least 1 h. Dimethylsulfate (Me$_2$SO$_4$) (2.67 mL, 28.17 mmol, 1.5 equiv) is added drop wise over 10 min. The reaction mixture is extracted with 15% ethyl acetate/heptane (3×75 mL), then the combined organic layers are concentrated down to 80 mL. Ethyl acetate (20 mL) is added and then washed with water (3×75 mL) and finally with brine (75 mL). The mixture is concentrated to an oil to afford the desired 1-Bromo-4-((E)-1-cyclopropyl-3-methoxy-1-methyl-3-phenyl-allyl)-benzene (7.5 g, 80.9 wt %, 87% yield).

2-(4-Bromo-phenyl)-2-cyclopropyl-propionic acid methyl ester

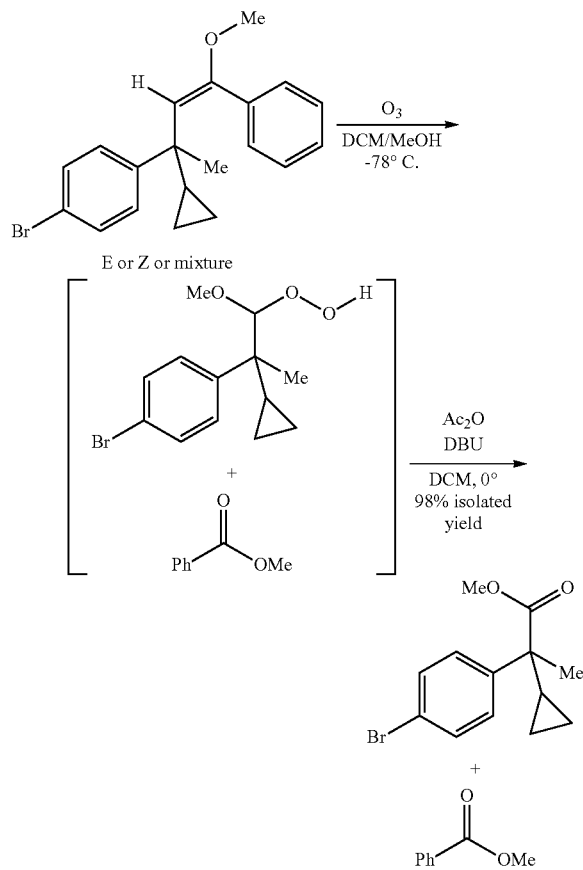

Ozonolysis:

A 250 mL reaction vessel is charged with (1-Bromo-4-((E)-1-cyclopropyl-3-methoxy-1-methyl-3-phenyl-allyl)-benzene (7.03 g, 80.94 wt %, 15.92 mmoles, 1 equiv). The vessel is purged with a flow of nitrogen. The vessel is charged with dichloromethane (50 mL, ACS grade, <0.01% H$_2$O) and methanol (10 mL, anhydrous). The colorless solution is cooled down to −78±5° C. The nitrogen flow is stopped and is replaced by a flow of oxygen (125 mL/min) that is bubbled into the solution through a medium gas dispersion frit. The ozonizer is turned on (60 µg/mL of ozone) for about 2.5-3 h and stopped right after a blue color appears and complete conversion of the methyl enol ether is observed by HPLC. Nitrogen is bubbled into the blue solution for about 15-20 min until the solution is colorless to remove any residual ozone. Meanwhile, the mixture is warmed to 15±5° C. over 30-45 min. Water (25 mL) is added to the reaction mixture and the layers are separated. The organic layer is washed with water (25 mL) once again and finally with aqueous NaCl$_{sat}$ (35 mL).

Dehydration:

The resulting mixture of 2-(4-Bromo-phenyl)-2-cyclopropyl-1-methoxy-prop-1-yl-hydroperoxide and methyl benzoate in dichloromethane is cooled down to about 0±5° C. 1,8-Diazabicycloundec-7-ene (DBU) (3.93 mL, 26.27 mmoles, 1.65 equiv) is added at 0±5° C. and the mixture is stirred for 5-10 min at that temperature. Acetic anhydride (Ac$_2$O) (4.51 mL, 47.77 mmoles, 3 equiv) is added and the reaction mixture is stirred for at least 25-30 min at 0±5° C. The mixture is then warmed to 20±5° C. over 40-60 min. The reaction mixture is quenched with aqueous HCl 10% v/v (35 mL) the layers are separated and the organic layer is then washed with HCl 10% v/v (35 mL) and finally with aqueous NaCl$_{sat}$ (35 mL). Solvent is distilled off to afford a 1:1 mixture (9.13 g) of 2-(4-Bromo-phenyl)-2-cyclopropyl-propionic acid methyl ester (47.2 wt %, 15.63 mmoles, 98% yield) and methyl benzoate (BIS0680) (19.3 wt %, 13 mmoles) as an oily residue.

2-(4-Bromo-phenyl)-2-cyclopropyl-propionic acid

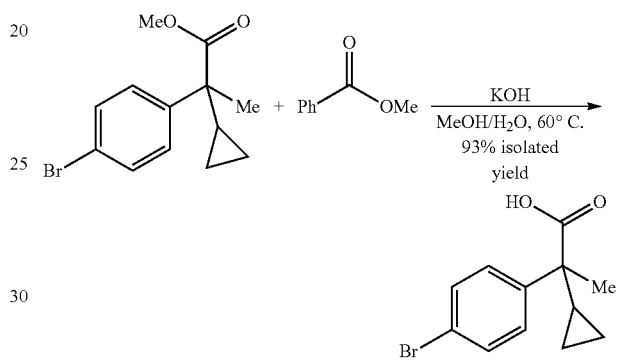

A 250 mL reaction vessel equipped with a condenser is charged with a mixture (9.18 g) of 2-(4-Bromo-phenyl)-2-cyclopropyl-propionic acid methyl ester (47.2 wt %, 15.3 mmoles, 1 equiv.) and methyl benzoate (19.3 wt %, 13 mmoles). The vessel is then charged with methanol (42 mL, ACS grade), water (8 mL, DI) and finally potassium hydroxide (KOH) (13.0 g, 12.7 equiv). The solution is then heated to 60±5° C. and allowed to stir for about 1.5 to 2.5 h. The colorless solution is cooled to 25±5° C. Methanol is distilled off to a minimum volume. The resulting heterogeneous mixture is acidified (pH=1) with concentrated HCl (16 mL, 37%), then extracted with methyl tert-butyl ether twice (35 mL). To the combined organic layer is added half saturated brine (40 mL). 4 N sodium hydroxide (NaOH) aqueous is added (1.6-2.3 equiv., 6-8.8 mL). The mixture is stirred for 5 min. Then the layers are separated. The organic layer is washed with brine 20 mL once and 1 N HCl 20 mL once and separated. It is concentrated to an oil to give 2-(4-Bromo-phenyl)-2-cyclopropyl-propionic acid (4.76 g). NMR assay showed 70.48 wt %; 81.4% yield.

2-(4-Bromo-phenyl)-2-cyclopropyl-propionic acid dicyclohexylamine salt

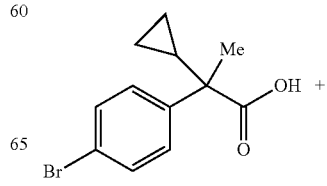

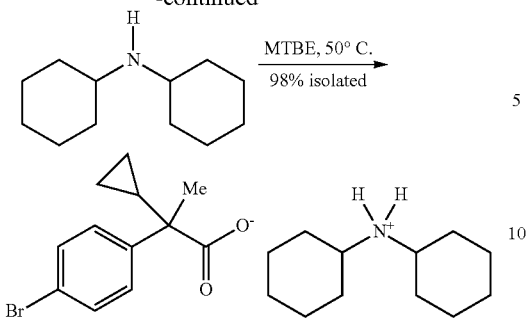

In a 250 mL flask equipped with a condenser, is charged with a solution of 2-(4-Bromo-phenyl)-2-cyclopropyl-propionic acid (5.00 g, 81.7 wt %, 15.18 mmol) and methyl tert-butyl ether (MTBE) (38 mL). Dicyclohexylamine (Cy$_2$NH) is charged (3.34 g, 99%, 18.21 mmol, 1.2 eq) at 20° C. There is a very moderate exotherm. A white sandy solid forms instantly. The mixture is heated to 50° C. for 0.5 h and then cooled to 20° C.

The slurry is filtered and the cake washed with MTBE (10 mL) and dried on the frit for 5-10 min to give a white solid 2-(4-Bromo-phenyl)-2-cyclopropyl-propionate dicyclohexyl-ammonium salt; (6.72 g, 98.3%). HPLC shows a single peak at 5.92 min. $^1$H NMR assay in CDCl$_3$ shows 97.9 wt %.

This salt may be further resolved to give to provide the corresponding optically pure enantiomers.

What is claimed is:

1. A process for preparing carboxylic acids of the formula XII or XIIA:

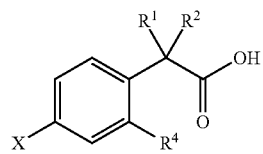

XII

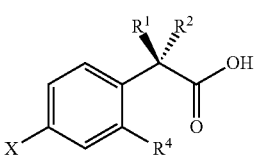

XIIA the process comprising:

a) reacting a carbonyl compound of formula XIII with a base and a C$_1$-C$_3$ alkylating agent, in a suitable solvent, to provide a compound of formula XIV:

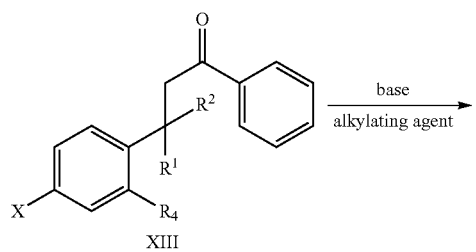

XIII

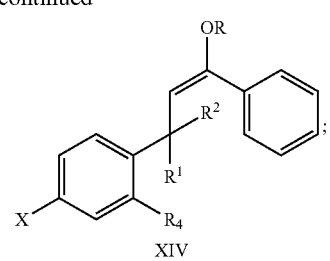

XIV b) reacting the compound of formula XIV with ozone, in a suitable solvent, followed by reaction with a dehydrating agent in the presence a base to provide an ester of formula XV;

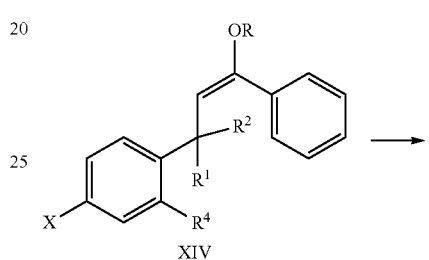

XIV

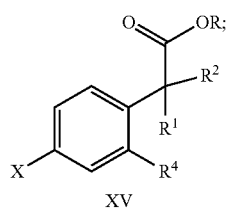

XV c) hydrolyzing the ester of formula XV, in a suitable solvent, in the presence of a suitable base, to provide an acid of formula XII:

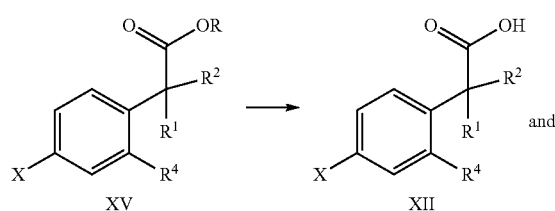

XV → XII  and d) optionally resolving the racemic acid of formula XII to provide the enantiomers XIIA and XIIA'

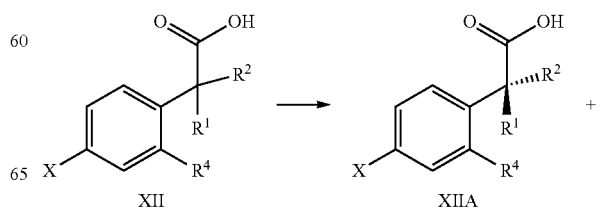

XII → XIIA  +

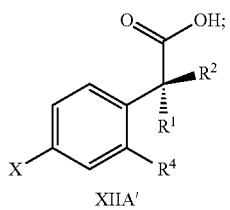

d') Alternatively, the acid XII obtained in step c) may be reacted with an organic base, such as a primary or secondary amine, in a suitable solvent, to provide the corresponding salt of formula XVI

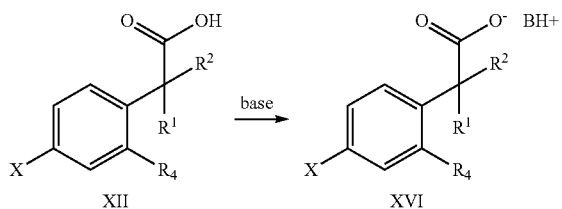

wherein:

R in step a) is a $C_{1-3}$ alkyl provided by the $C_1$-$C_3$ alkylating agent;

$R^1$ and $R^2$ are each independently hydrogen, $C_{1-7}$ alkyl or $C_{3-10}$ carbocycle, with the proviso that both $R^1$ and $R^2$ are not hydrogen;

$R^4$ is hydrogen, $C_{1-3}$ alkyl, halogen or nitrile; and

X is halogen;

B in step d') is a primary or secondary amine.

2. The process according to claim 1, wherein:
the base in step (a) is selected from the group consisting of potassium t-butoxide, sodium t-butoxide, lithium t-butoxide, sodium hydride, potassium hydride, lithium hydride, sodium hexamethyldisilazide, potassium hexamethyldisilazide, lithium hexamethyldisilazide, sodium methoxide, potassium methoxide, lithium methoxide, sodium ethoxide, potassium ethoxide, lithium ethoxide, LDA, n-butyllithium, sec-butyllithium and t-butyllithium.

3. The process according to claim 1, wherein:
the solvent in step (a) is selected from a group consisting of dimethylformamide, dichloromethane, ethyl acetate, hexane, heptane, acetonitrile, methyl tert-butyl ether, isopropyl acetate, toluene, and cyclopropylmethyl ether.

4. The process according to claim 1, wherein:
the alkylating agent in step (a) is selected from a group consisting of dimethyl sulfate, dimethyl carbonate, bromomethane, methyl trifluoromethanesulfonate and iodomethane.

5. The process according to claim 1, wherein:
the solvent in step (b) is selected from a group consisting of dimethylformamide, dichloromethane, ethyl acetate, hexane, heptane, acetonitrile, methyl tert-butyl ether, isopropyl acetate, toluene, and cyclopropylmethyl ether.

6. The process according to claim 1, wherein:
the base in step (b) is selected from a group consisting of 1,8-diazabicycloundec-7-ene (DBU), triethylamine, pyridine, 4-methylmorpholine, diisopropylethylamine and dimethylamine.

7. The process according to claim 1, wherein:
the dehydrating agent in step (b) is selected from a group consisting of acetic anhydride, methanesulfonyl chloride, trifluoroacetic anhydride, toluenesulfonyl chloride, sodium hypochlorite, calcium hypochlorite and tert-butyl hypochlorite.

8. The process according to claim 1, wherein:
the base in step (c) is selected from a group consisting of potassium hydroxide, sodium hydroxide, lithium hydroxide and cesium hydroxide.

9. The process according to claim 1, wherein:
the solvent in step (c) is selected from a group consisting of methanol, methanol-water mixture, dimethylformamide, dichloromethane, ethyl acetate, hexane, heptane, acetonitrile, methyl tert-butyl ether, isopropyl acetate, toluene, and cyclopropylmethyl ether.

* * * * *